(12) United States Patent
Ross et al.

(10) Patent No.: US 10,271,848 B2
(45) Date of Patent: *Apr. 30, 2019

(54) END EFFECTOR IDENTIFICATION BY MECHANICAL FEATURES

(71) Applicant: Covidien LP, Mansfield, MA (US)

(72) Inventors: Adam Ross, Prospect, CT (US);
Michael Zemlok, Prospect, CT (US);
Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 754 days.

This patent is subject to a terminal disclaimer.

(21) Appl. No.: 14/689,441

(22) Filed: Apr. 17, 2015

(65) Prior Publication Data

US 2015/0223815 A1 Aug. 13, 2015

Related U.S. Application Data

(63) Continuation of application No. 14/282,724, filed on May 20, 2014, now Pat. No. 9,010,611, which is a
(Continued)

(51) Int. Cl.
*A61B 17/10* (2006.01)
*A61B 17/068* (2006.01)
(Continued)

(52) U.S. Cl.
CPC .......... *A61B 17/105* (2013.01); *A61B 17/068* (2013.01); *A61B 17/072* (2013.01);
(Continued)

(58) Field of Classification Search
CPC .... A61B 17/07207; A61B 2017/00017; A61B 17/105; A61B 2090/061; A61B 17/0686
(Continued)

(56) References Cited

U.S. PATENT DOCUMENTS 4,058,079 A * 11/1977 Taylor ................ E21D 21/0093
116/283
4,705,038 A 11/1987 Sjostrom et al.
(Continued)

FOREIGN PATENT DOCUMENTS

CN 101283924 A 10/2008
CN 101401736 A 4/2009
(Continued)

OTHER PUBLICATIONS

European Communication, dated Aug. 2, 2016, corresponding to European Application No. 15 151 410.6; 6 pages.
(Continued)

*Primary Examiner* — Robert Long

(57) ABSTRACT

According to one aspect of the present disclosure, a surgical instrument is disclosed. The instrument includes a handle portion, a body portion extending distally from the handle portion and defining a first longitudinal axis and a loading unit. The loading unit includes a tool assembly, the loading adapted to be coupled to the body portion. The instrument also includes a sensor tube movably positioned within the body portion, the sensor tube adapted to engage the loading unit and a load switch coupled to a microcontroller. The load switch is adapted to be actuated by the sensor tube when the sensor tube is engaged by the loading unit being inserted into the body portion.

13 Claims, 8 Drawing Sheets

Related U.S. Application Data continuation of application No. 12/773,176, filed on May 4, 2010, now Pat. No. 8,733,614, which is a continuation-in-part of application No. 12/345,167, filed on Dec. 29, 2008, now Pat. No. 7,815,090, which is a continuation of application No. 11/544,203, filed on Oct. 6, 2006, now Pat. No. 7,481,348, said application No. 12/773,176 is a continuation of application No. 12/189,834, filed on Aug. 12, 2008, now abandoned.

(60) Provisional application No. 61/225,377, filed on Jul. 14, 2009, provisional application No. 60/997,854, filed on Oct. 5, 2007.

(51) Int. Cl.
| | |
|---|---|
| *A61B 17/072* | (2006.01) |
| *A61B 90/98* | (2016.01) |
| *A61B 17/00* | (2006.01) |
| *A61B 17/29* | (2006.01) |
| *A61B 17/32* | (2006.01) |
| *A61B 90/00* | (2016.01) |

(52) U.S. Cl.
CPC ........ *A61B 17/07207* (2013.01); *A61B 90/98* (2016.02); *A61B 2017/00017* (2013.01); *A61B 2017/0046* (2013.01); *A61B 2017/00398* (2013.01); *A61B 2017/00473* (2013.01); *A61B 2017/00482* (2013.01); *A61B 2017/00725* (2013.01); *A61B 2017/00734* (2013.01); *A61B 2017/2927* (2013.01); *A61B 2017/320052* (2013.01); *A61B 2090/0808* (2016.02); *A61B 2562/00* (2013.01)

(58) Field of Classification Search
USPC ...... 227/175.1–182.1; 606/75, 300, 138, 219
See application file for complete search history.

(56) References Cited

U.S. PATENT DOCUMENTS

| | | | |
|---|---|---|---|
| 5,312,023 | A | 5/1994 | Green et al. |
| 5,318,221 | A | 6/1994 | Green et al. |
| 5,326,013 | A | 7/1994 | Green et al. |
| 5,359,894 | A * | 11/1994 | Saito ................ G01P 15/11 336/30 |
| 5,364,001 | A | 11/1994 | Bryan |
| 5,487,499 | A | 1/1996 | Sorrentino et al. |
| 5,526,822 | A | 6/1996 | Burbank et al. |
| 5,529,235 | A * | 6/1996 | Boiarski ........ A61B 17/07207 227/175.1 |
| 5,620,479 | A | 4/1997 | Diederich |
| 5,669,544 | A | 9/1997 | Schulze et al. |
| 5,673,841 | A | 10/1997 | Schulze et al. |
| 5,680,982 | A | 10/1997 | Schulze et al. |
| 5,692,668 | A | 12/1997 | Schulze et al. |
| 5,865,361 | A | 2/1999 | Milliman et al. |
| 5,918,791 | A | 7/1999 | Sorrentino et al. |
| 6,010,054 | A | 1/2000 | Johnson et al. |
| 6,079,606 | A | 6/2000 | Milliman et al. |
| 6,241,139 | B1 | 6/2001 | Milliman et al. |
| 6,250,532 | B1 | 6/2001 | Green et al. |
| 6,330,965 | B1 | 12/2001 | Milliman et al. |
| 6,669,073 | B2 | 12/2003 | Milliman et al. |
| 6,830,174 | B2 | 12/2004 | Hillstead et al. |
| 6,840,938 | B1 * | 1/2005 | Morley ............ A61B 18/1445 606/50 |
| 6,905,057 | B2 | 6/2005 | Swayze et al. |
| 6,918,580 | B2 | 7/2005 | Obregon et al. |
| 6,953,139 | B2 | 10/2005 | Milliman et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 7,000,819 | B2 | 2/2006 | Swayze et al. |
| 7,055,731 | B2 | 6/2006 | Shelton, IV et al. |
| 7,059,508 | B2 | 6/2006 | Shelton, IV et al. |
| 7,083,075 | B2 | 8/2006 | Swayze et al. |
| 7,111,769 | B2 | 9/2006 | Wales et al. |
| 7,128,254 | B2 | 10/2006 | Shelton, IV et al. |
| 7,140,528 | B2 | 11/2006 | Shelton, IV |
| 7,143,925 | B2 | 12/2006 | Shelton, IV et al. |
| 7,143,926 | B2 | 12/2006 | Shelton, IV et al. |
| 7,246,734 | B2 | 7/2007 | Shelton, IV |
| 7,328,828 | B2 | 2/2008 | Ortiz et al. |
| 7,364,061 | B2 | 4/2008 | Swayze et al. |
| 7,380,696 | B2 | 6/2008 | Shelton, IV et al. |
| 7,404,508 | B2 | 7/2008 | Smith et al. |
| 7,416,101 | B2 | 8/2008 | Shelton, IV et al. |
| 7,419,080 | B2 | 9/2008 | Smith et al. |
| 7,422,136 | B1 * | 9/2008 | Marczyk ........ A61B 17/07207 227/175.1 |
| 7,422,139 | B2 | 9/2008 | Shelton, IV et al. |
| 7,431,188 | B1 | 10/2008 | Marczyk |
| 7,431,189 | B2 | 10/2008 | Shelton, IV et al. |
| 7,434,715 | B2 | 10/2008 | Shelton, IV et al. |
| 7,441,684 | B2 | 10/2008 | Shelton, IV et al. |
| 7,448,525 | B2 | 11/2008 | Shelton, IV et al. |
| 7,464,846 | B2 | 12/2008 | Shelton, IV et al. |
| 7,464,849 | B2 | 12/2008 | Shelton, IV et al. |
| 7,481,348 | B2 | 1/2009 | Marczyk |
| 7,487,899 | B2 | 2/2009 | Shelton, IV et al. |
| 7,549,563 | B2 | 6/2009 | Mather et al. |
| 7,552,854 | B2 | 6/2009 | Wixey et al. |
| 7,568,603 | B2 | 8/2009 | Shelton, IV et al. |
| 7,641,093 | B2 | 1/2010 | Doll et al. |
| 7,644,848 | B2 | 1/2010 | Swayze et al. |
| 7,670,334 | B2 | 3/2010 | Hueil et al. |
| 7,717,312 | B2 | 5/2010 | Beetel |
| 7,721,931 | B2 | 5/2010 | Shelton, IV et al. |
| 7,740,159 | B2 | 6/2010 | Shelton, IV et al. |
| 7,766,207 | B2 | 8/2010 | Mather et al. |
| 7,766,210 | B2 | 8/2010 | Shelton, IV et al. |
| 7,770,775 | B2 | 8/2010 | Shelton, IV et al. |
| 7,845,537 | B2 | 12/2010 | Shelton, IV et al. |
| 7,922,063 | B2 | 4/2011 | Zemlok et al. |
| 7,954,682 | B2 | 6/2011 | Giordano et al. |
| 8,105,233 | B2 * | 1/2012 | Abou El Kheir .... A61B 1/0008 348/47 |
| 8,201,721 | B2 | 6/2012 | Zemlok et al. |
| 8,652,120 | B2 * | 2/2014 | Giordano ............... A61B 17/00 606/1 |
| 8,733,614 | B2 | 5/2014 | Ross et al. |
| 8,800,839 | B2 | 8/2014 | Beetel |
| 9,010,611 | B2 | 4/2015 | Ross et al. |
| 2002/0165541 | A1 | 11/2002 | Whitman |
| 2003/0208103 | A1 * | 11/2003 | Sonnenschein .... A61B 1/00154 600/117 |
| 2004/0106937 | A1 * | 6/2004 | Berube ................ A61B 17/122 606/151 |
| 2004/0232201 | A1 | 11/2004 | Wenchell et al. |
| 2005/0100867 | A1 | 5/2005 | Hilscher et al. |
| 2005/0131390 | A1 | 6/2005 | Heinrich et al. |
| 2006/0045235 | A1 * | 3/2006 | Bruder .................. A61B 6/032 378/9 |
| 2006/0273135 | A1 * | 12/2006 | Beetel .................. A61B 17/068 227/175.1 |
| 2007/0023477 | A1 | 2/2007 | Whitman et al. |
| 2007/0084897 | A1 | 4/2007 | Shelton et al. |
| 2007/0085496 | A1 * | 4/2007 | Philipp ................ A61B 17/151 318/139 |
| 2007/0108931 | A1 * | 5/2007 | Bellingroth ........ F16H 25/2015 318/466 |
| 2007/0152802 | A1 | 7/2007 | Knoll et al. |
| 2007/0175949 | A1 | 8/2007 | Shelton et al. |
| 2007/0175950 | A1 | 8/2007 | Shelton et al. |
| 2007/0175951 | A1 | 8/2007 | Shelton et al. |
| 2007/0175953 | A1 | 8/2007 | Shelton et al. |
| 2007/0175955 | A1 | 8/2007 | Shelton et al. |
| 2007/0175964 | A1 | 8/2007 | Shelton et al. |
| 2007/0249901 | A1 | 10/2007 | Ohline et al. |

(56) References Cited

U.S. PATENT DOCUMENTS

| | | |
|---|---|---|
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0167671 A1 | 7/2008 | Giordano et al. |
| 2008/0249551 A1 | 10/2008 | Sunaoshi et al. |
| 2009/0090763 A1 | 4/2009 | Zemlok et al. |
| 2009/0095790 A1* | 4/2009 | Whitman ......... A61B 17/07207 227/175.1 |
| 2009/0101694 A1 | 4/2009 | Marczyk |
| 2010/0096435 A1 | 4/2010 | Fuchs et al. |
| 2010/0211053 A1 | 8/2010 | Ross et al. |
| 2012/0078222 A1 | 3/2012 | Smith et al. |
| 2017/0281174 A1* | 10/2017 | Harris ............. A61B 17/07207 |

FOREIGN PATENT DOCUMENTS

| | | |
|---|---|---|
| EP | 0 537 570 A2 | 4/1993 |
| EP | 0 647 431 A2 | 4/1995 |
| EP | 0 738 501 A1 | 10/1996 |
| EP | 1728475 A2 | 12/2006 |
| EP | 1 769 754 A1 | 4/2007 |
| EP | 1 813 203 A2 | 8/2007 |
| EP | 1980215 A2 | 10/2008 |
| EP | 2044890 A1 | 4/2009 |
| WO | 03/026511 A1 | 4/2003 |
| WO | 03/030743 A2 | 4/2003 |

OTHER PUBLICATIONS

Canadian Office Action and Examination Search Report dated Nov. 15, 2016, corresponding to Canadian Application No. 2,708,867; 5 total pages.

European Communication dated Mar. 13, 2017, correspnding to European Application No. 15 151 410.6; 4 total pages.

European extended European Search Report, dated Jun. 25, 2015, corresponding to European Patent Application No. 15151410.6; 8 pages.

European Search Report dated Jul. 28, 2011 for EP 11 15 2266.

European Search Repon dated Apr. 17, 2007 for Corresponding Patent Application EP06026840.

International Search Report for corresponding PCT Application—PCT/US06/21524—dated May 28, 2008 (4 Pages).

Detemple, P., "Microtechnology in Modem Health Care", Med Device Technol. 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for Corresponding EP 08251357 dated Sep. 29. 2009 (3 pages).

Chinese Office Action (with English translation), corresponding to Chinese Application No. 201410642696.8, dated Mar. 4, 2016; 14 pages.

\* cited by examiner

END EFFECTOR IDENTIFICATION BY MECHANICAL FEATURES

CROSS-REFERENCE TO RELATED APPLICATIONS

The present application is a continuation application of U.S. application Ser. No. 14/282,724 filed on May 20, 2014, which is a continuation application of U.S. application Ser. No. 12/773,176 filed on May 4, 2010 (now U.S. Pat. No. 8,733,614), which claims the benefit of and priority to U.S. Provisional Application Ser. No. 61/225,377 filed on Jul. 14, 2009 and is a continuation-in-part application of U.S. application Ser. No. 12/345,167 filed on Dec. 29, 2008 (now U.S. Pat. No. 7,815,090), which is a continuation application of U.S. application Ser. No. 11/544,203 filed on Oct. 6, 2006 (now U.S. Pat. No. 7,481,348). U.S. application Ser. No. 12/773,176 is also a continuation of U.S. application Ser. No. 12/189,834 filed on Aug. 12, 2008, (now abandoned), which claims priority to a U.S. Provisional Application Ser. No. 60/997,854 filed on Oct. 5, 2007, the entire contents of all of which are hereby incorporated by reference herein.

BACKGROUND

Technical Field

The present disclosure relates to a surgical instrument adapted to be coupled to removable loading units having various end effectors. More particularly, the present disclosure relates to a surgical instrument which includes a mechanism for identifying the type of an end effector mounted to the loading unit.

Background of Related Art

Surgical instruments which include a tool assembly mounted on a distal end of a body portion of the surgical instrument for articulation are well known. Typically, such surgical instruments include articulation control mechanisms which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through a small incision in the body to access a surgical site. Typically, an appropriately sized cannula, e.g., 5 mm, 10 mm, etc., is inserted through the body incision to provide a guide channel for accessing the surgical site.

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are known in the art. Certain of these instruments utilize a pressurized gas supply which connects to a trigger mechanism. The trigger mechanism, when depressed, simply releases pressurized gas to implant a fastener into tissue.

Motor-powered surgical staplers are also known in the art. These include powered surgical staplers having motors which activate staple firing mechanisms. However, these motor powered devices only provide for limited user control of the stapling process. The user can only toggle a single switch and/or button to actuate the motor and applies corresponding torque to the stapler's firing mechanisms. In certain other devices, a controller is used to control the stapler.

There is a continual need for new and improved powered surgical staplers which include various sensors. The sensors provide relevant feedback to feedback controllers which automatically adjust various parameters of the powered stapler in response to sensed feedback signals representative of stapler operation, including articulation and actuation of the tool assemblies.

SUMMARY

According to one aspect of the present disclosure, a surgical instrument is disclosed. The instrument includes a handle portion, a body portion extending distally from the handle portion and defining a first longitudinal axis and a loading unit. The loading unit includes a tool assembly, the loading adapted to be coupled to the body portion. The instrument also includes a sensor tube movably positioned within the body portion, the sensor tube adapted to engage the loading unit and a load switch coupled to a microcontroller. The load switch is adapted to be actuated by the sensor tube when the sensor tube is engaged by the loading unit being inserted into the body portion.

According to another aspect of the present disclosure, a surgical instrument is disclosed. The instrument includes a handle portion and a body portion extending distally from the handle portion and defining a first longitudinal axis. The body portion includes a distal end adapted to releasably engage both articulating and non-articulating loading unit types. The instrument also includes an articulation mechanism configured to articulate an articulating tool assembly coupled to an articulating loading unit and a sensor tube movably positioned within the body portion. The sensor tube is adapted to engage the articulating loading unit. The instrument further includes a load switch coupled to a microcontroller and adapted to be actuated by the sensor tube when the sensor tube is engaged by the articulating loading unit, wherein upon actuation the load switch signals the microprocessor to activate the articulation mechanism.

According to a further embodiment of the present disclosure a surgical instrument is disclosed. The instrument includes a handle portion and a body portion extending distally from the handle portion and defining a first longitudinal axis. The body portion includes a distal end adapted to releasably engage a plurality of loading unit types. The instrument also includes a sensor tube movably positioned within the body portion, the sensor tube adapted to engage each of the plurality of loading unit types and to move a predetermined distance in response thereto; and a variable loading unit sensor adapted to determine a type of a loading unit engaged with the body portion based on the predetermined distance the sensor tube has been displaced.

BRIEF DESCRIPTION OF THE DRAWINGS

Various embodiments of the subject instrument are described herein with reference to the drawings wherein.

DETAILED DESCRIPTION

Figure 1:
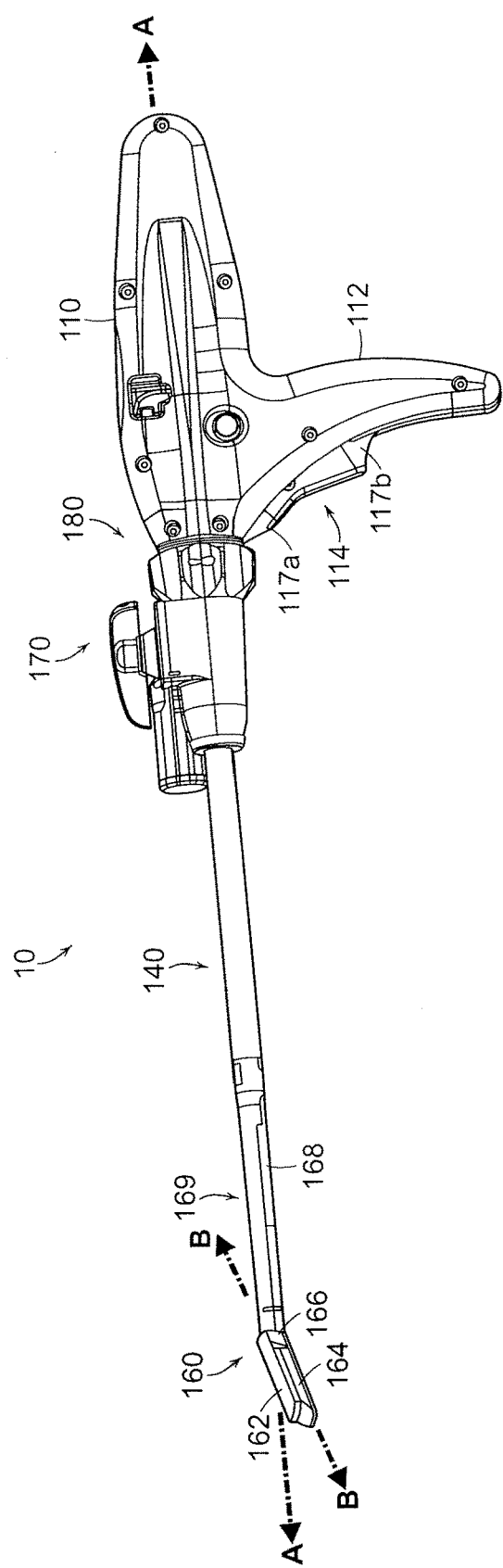
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 10. Referring initially to FIG. 1, powered surgical instrument 10 includes a housing 110, a body portion, such as, for example, an endoscopic portion 140 defining a first longitudinal axis A-A extending therethrough, and a loading unit 169. Loading unit 169 includes a proximal body portion 168 and an articulating tool assembly (e.g., end effector 160), defining a second longitudinal axis B-B extending therethrough. Endoscopic portion 140 extends distally from housing 110 and proximal body portion 168 of loading unit 169 is disposed adjacent a distal portion of endoscopic portion 140. In an embodiment, the components of the housing 110 are sealed against infiltration of particulate and/or fluid contamination and help prevent damage of the components by sterilization processes.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position, in which the anvil assembly 162 is spaced from cartridge assembly 164, and an approximated or clamped position, in which the anvil assembly 162 is in juxtaposed alignment with cartridge assembly 164.

It is further envisioned that end effector 160 is attached to a mounting portion 166, which is pivotably attached to proximal body portion 168. Proximal body portion 168 may be integral with endoscopic portion 140 of powered surgical instrument 10, or may be removably attached to the instrument 10 such that loading unit 169 is in the form of a replaceable, disposable loading unit (DLU) or single use loading unit (SULU). In certain embodiments, the reusable portion may be configured for sterilization and re-use in a subsequent surgical procedure.

A proximal end of proximal body portion 168 of loading unit 169 may be connectable to endoscopic portion 140 through a bayonet connection. It is envisioned that a distal end of proximal body portion 168 of loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A as discussed in more detail below. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, graspers, etc. Such end effectors may be coupled to endoscopic portion 140 of powered surgical instrument 10. An intermediate flexible shaft may be included between handle portion 112 and loading unit. It is envisioned that the incorporation of a flexible shaft may facilitate access to and/or within certain areas of the body.

Figure 2:
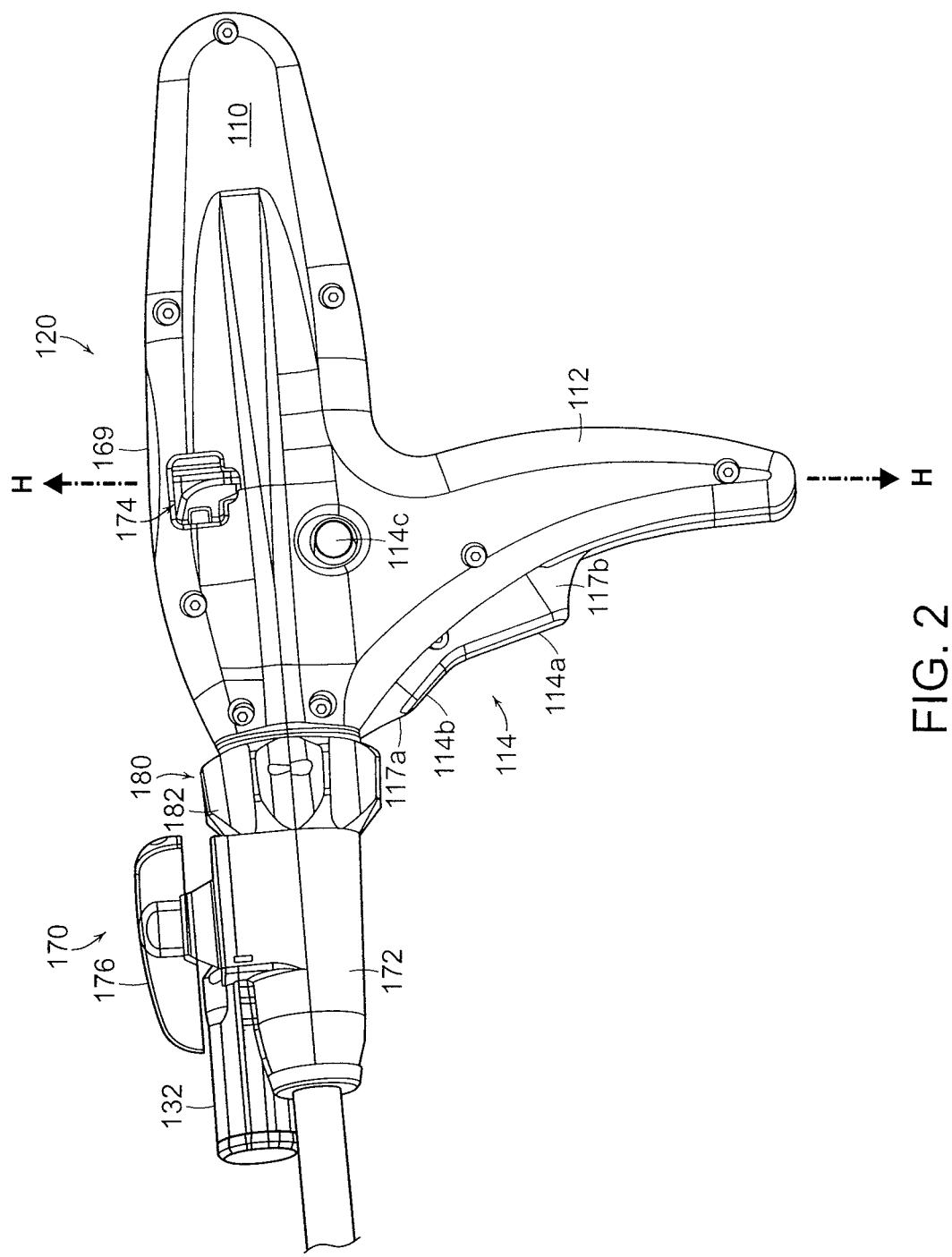
FIG. 2 is a partial enlarged perspective view of the powered surgical instrument of FIG. 1 according to the embodiment of the present disclosure.

With reference to FIGS. 1 and 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers.

Figure 4:
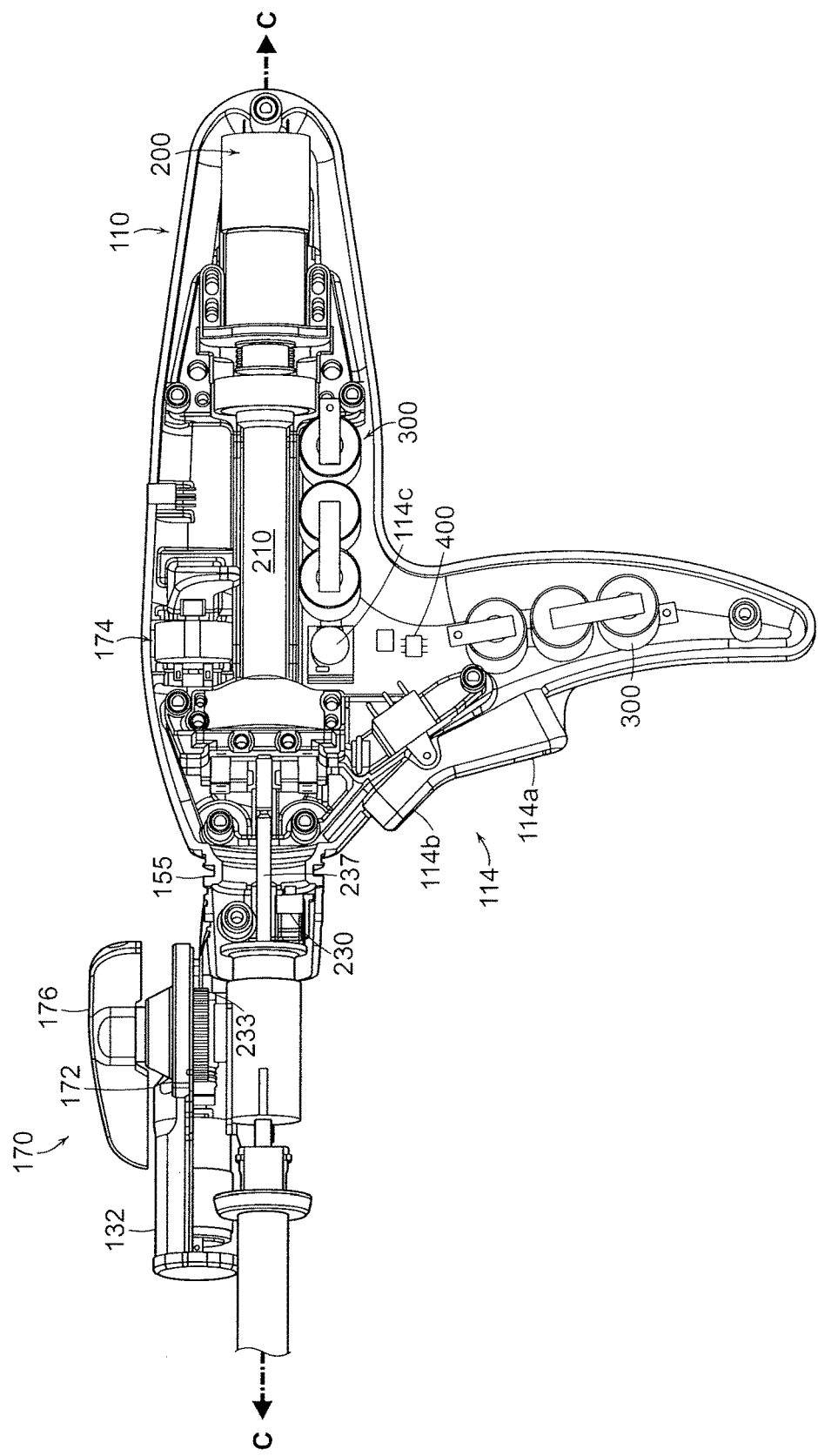
FIG. 4 is a partial sectional view of internal components of the powered surgical instrument of FIG. 1 in accordance with an embodiment of the present disclosure.

Additionally, and with reference to FIGS. 1 and 2, switches 114a, 114b may be used for starting and/or stopping movement of drive motor 200 (FIG. 4). In one embodiment, the switch 114a is configured to activate the drive motor 200 in a first direction to advance firing rod (not explicitly shown) in a distal direction thereby approximating the anvil and the cartridge assemblies 162 and 164. Conversely, the switch 114b may be configured to retract the firing rod to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shield 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod in a non-linear manner. For example, switches 114a, 114b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch 114c is pressed.

The switches 114a and 114b are coupled to a non-linear speed control circuit which can be implemented as a voltage regulation circuit, a variable resistance circuit, or a microelectronic pulse width modulation circuit. The switches 114a and 144b may interface with the control circuit by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as gradually increasing the speed of the drive motor 200 either incrementally or gradually depending on the type of the control circuit being used, based on the depression of the switches 114a and 114b.

Figure 3:
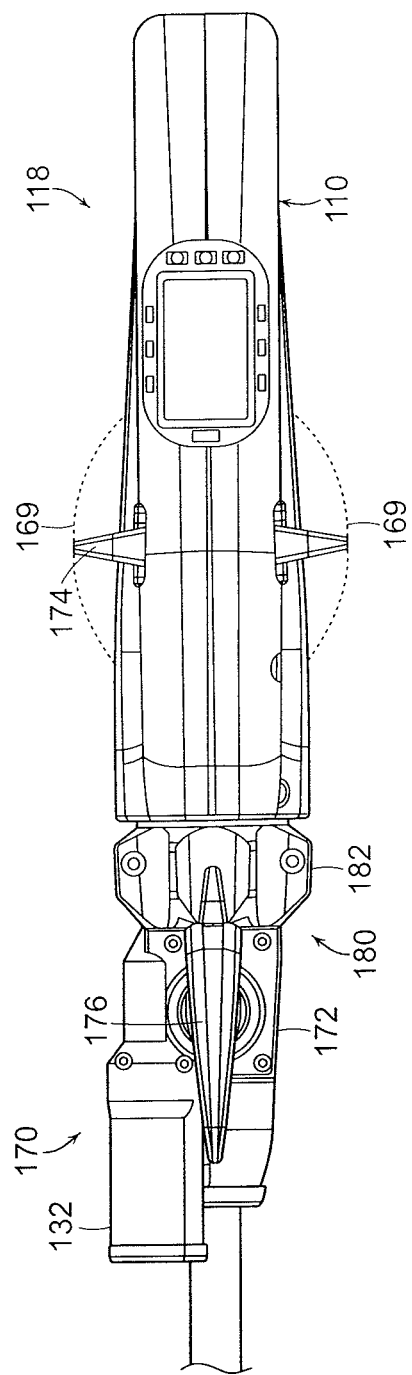
FIG. 3 is a partial enlarged plan view of the powered surgical instrument of FIG. 1 according to the embodiment of the present disclosure.

FIGS. 2-4 illustrate an articulation mechanism 170, including an articulation housing 172, a powered articulation switch 174, an articulation motor 132 and a manual articulation knob 176. Translation of the powered articulation switch 174 activates the articulation motor 132 which then actuates an articulation gear 233 of the articulation mechanism 170 as shown in FIG. 4. Pivoting of the manual articulation knob 176 bypasses the articulation motor 132 to actuate the articulation mechanism 170. The manual articulation knob 176 also provides an indication of the angulation of the end effector 160 with respect to longitudinal axis A-A. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. The powered articulation switch 174 may also incorporate similar non-linear speed controls as the clamping mechanism. These can be controlled by the switches 114a and 114b.

With reference to FIGS. 2 and 3, the housing 110 includes switch shields 167 having a wing-like shape and extending from the top surface of the housing 110 over the switch 174. The switch shields 167 prevent accidental activation of the switch 174 and require the user to reach below the shield 167 in order to activate the articulation mechanism 170.

Additionally, articulation housing 172 and manual articulation knob 176 are mounted to a rotating housing assembly 180. Rotation of a rotation knob 182 about first longitudinal axis A-A causes housing assembly 180 as well as articulation housing 172 and manual articulation knob 176 to rotate about first longitudinal axis A-A, and thus causes corresponding rotation of distal portion 224 of firing rod 220 and end effector 160 about first longitudinal axis A-A. The articulation mechanism 170 is electro-mechanically coupled to one or more conductive rings that are disposed on a housing nose assembly 155 (FIG. 4). The conductive rings may be soldered and/or crimped onto the nose assembly 155 and are in electrical contact with a power source 300 thereby providing electrical power to the articulation mechanism 170. The nose assembly 155 may be modular and may be attached to the housing 110 during assembly to allow for easier soldering and/or crimping of the rings. The articulation mechanism 170 may include one or more brush and/or spring loaded contacts in contact with the conductive rings such that as the housing assembly 180 is rotated along with the articulation housing 172 the articulation mechanism 170 is in continuous contact with the conductive rings thereby receiving electrical power from the power source 300.

Further details of articulation housing 172, powered articulation switch 174, manual articulation knob 176 and providing articulation to end effector 160 are described in detail in commonly-owned U.S. Pat. No. 7,431,188, the contents of which are hereby incorporated by reference in their entirety. It is envisioned that any combinations of limit switches, proximity sensors (e.g., optical and/or ferromagnetic), linear variable displacement transducers and shaft encoders which may be disposed within housing 110, may be utilized to control and/or record an articulation angle of end effector 160 and/or position of the firing rod 220.

As shown in FIG. 4, the instrument 10 also includes a microcontroller 400 electrically coupled to the motor 200 and various sensors disposed in the instrument 10. The sensors detect various operating parameters of the instrument 10 (e.g., linear speed, rotation speed, articulation position, temperature, battery charge, and the like), which are then reported to the microcontroller 400. The microcontroller 400 may then respond accordingly to the measured operating parameters (e.g., adjust the speed of the motor 200, control articulation angle, shut-off the power supply, report error conditions, etc.).

With continued reference to FIG. 4, a load switch 230 is disposed within the articulation housing 172. The switch 230 is connected in series with the switch 114, preventing activation of the instrument 10 unless the loading unit 169 is properly loaded into the instrument 10. If the loading unit 169 is not loaded into the instrument 10, the main power switch (e.g., switch 114) is open, thereby preventing use of any electronic or electric components of the instrument 10. This also prevents any possible current draw from the power source 300 allowing the power source 300 to maintain a maximum potential over its specified shelf life.

Thus, the switch 230 acts as a so-called "lock-out" switch which prevents false activation of the instrument 10 since the switch 230 is inaccessible to external manipulation and can only be activated by the insertion of the loading unit 169. The switch 230 is activated by displacement of a plunger or sensor tube 360 as the loading unit 169 is inserted into the endoscopic portion 140. Once the switch 230 is activated, the power from the power source 300 is supplied to the electronic components (e.g., sensors, microcontroller 400, etc.) of the instrument 10 providing the user with access to a user interface and other inputs/outputs.

Figure 5:
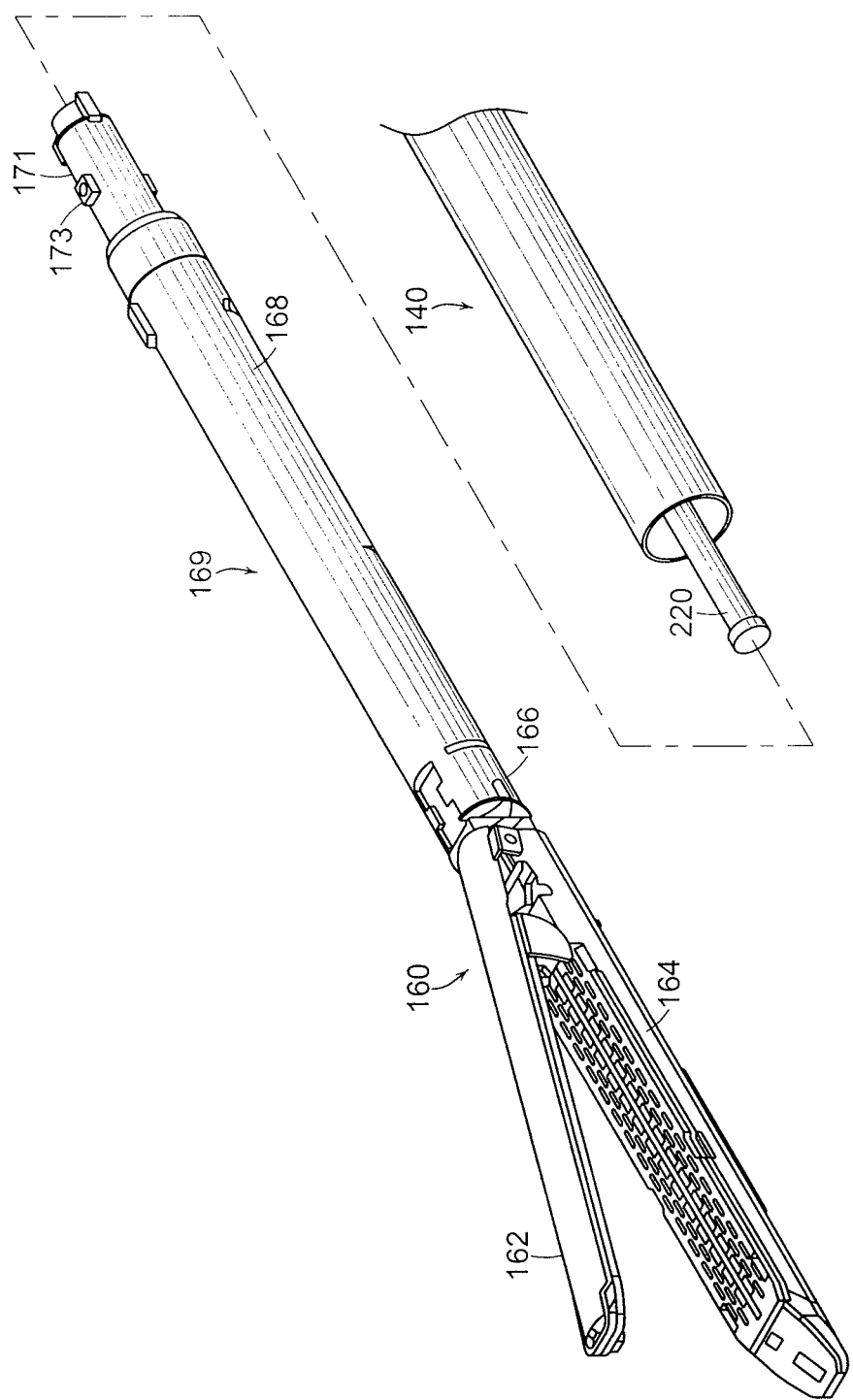
FIG. 5 is a perspective view of a loading unit according to one embodiment of the present disclosure.
Figure 6:
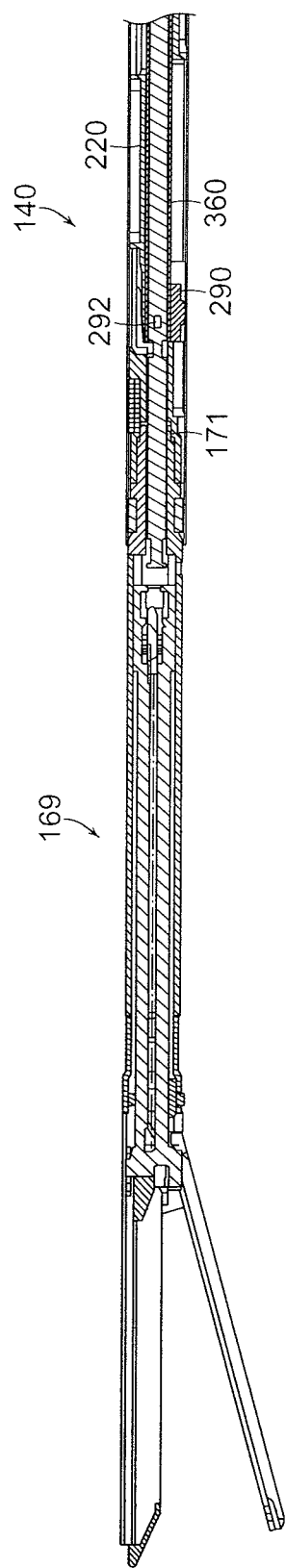
FIG. 6 is a partial sectional view of internal components of the loading unit and the powered surgical instrument of FIG. 1 according to the embodiment of the present disclosure.
Figure 7:
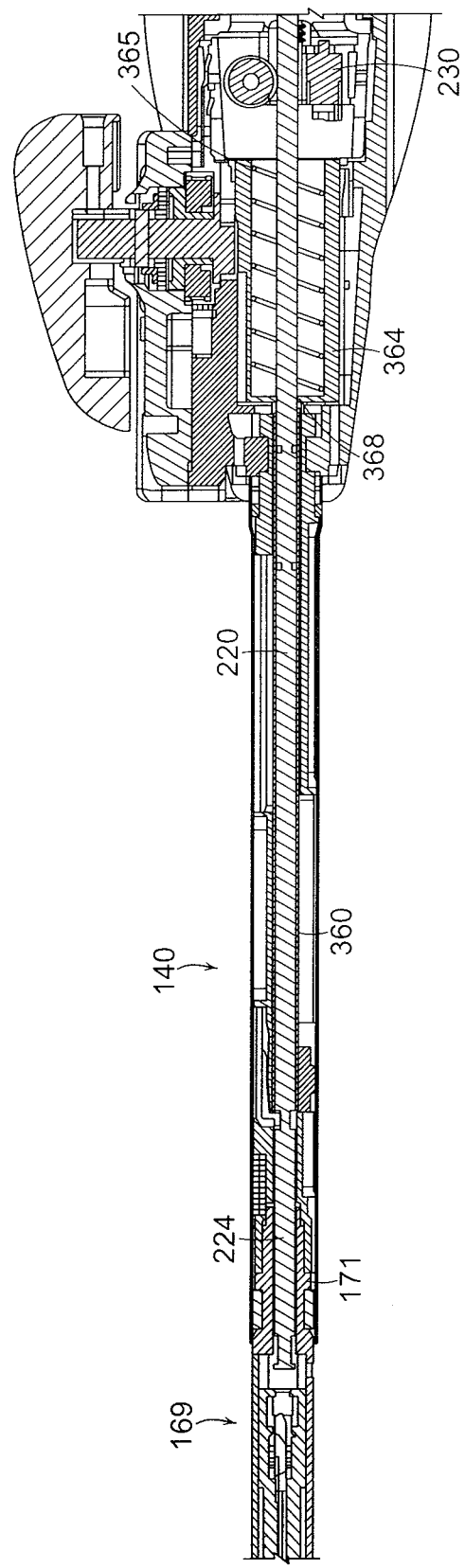
FIG. 7 is a partial sectional view of internal components of the loading unit and the powered surgical instrument of FIG. 1 according to the embodiment of the present disclosure.

As shown in FIGS. 5-7, the endoscopic portion 140 includes the sensor tube 360 (FIG. 6) therein disposed around the firing rod 220. The firing rod 220 passes through an opening 368 at a distal end of a sensor cap 364 (FIG. 7). The sensor cap 364 includes a spring 365 and abuts the switch 230. The sensor cap 364 is biased against the sensor tube 360, which is in contact with the distal end of the sensor cap 364.

As shown in FIGS. 5 and 6, when the loading unit 169 is loaded into the endoscopic portion 140, the proximal portion 171 abuts the sensor tube 360, which displaces the sensor tube 360 in a proximal direction. With reference to FIG. 7, the sensor tube 360 then pushes on the sensor cap 364 in the proximal direction, which then compresses the spring 365 and activates the switch 230 denoting that the loading unit 169 has been properly inserted.

Once the loading unit 169 is inserted into the endoscopic portion, the switch 230 also determines whether the loading unit 169 is loaded correctly based on the position thereof. If the loading unit 169 is improperly loaded, the switch 114 is not activated and an error code is relayed to the user.

In another embodiment, the switch 230 may be adapted to sense the type of a disposable loading unit 169 (e.g., articulating vs. non-articulating) engaged with the endoscopic portion 140. When a non-articulating loading unit is used, the sensor tube 360 is not engaged and the sensor cap 364 does not activate the switch 230. The switch 230 may still allow for operation of the instrument 10, but prevent operation of the articulation mechanism 170. When an articulating loading unit 169 is used, the sensor tube 360 is engaged and the sensor cap 364 activates the switch 230. The switch 230 allows for operating of the instrument 10 including the articulation mechanism 170. The articulating and non-articulating loading units may be distinguished by a protrusion 173 (FIG. 5) or extended insertion tip (not explicitly shown) that when present, is configured to engage the sensor tube 360. In other words, non-articulating loading units do not have a protrusion 173 for engaging the sensor tube 360 and thus do not activate the switch 230, whereas the articulating loading units 169 include the protrusion 173 and can thus enable operation of the articulation mechanism 169. Thus, the sensor tube 360 is movable to a first position or is not moved at all in response to engagement with a non-articulating loading unit and is movable to a second position in response to engagement of an articulating loading unit 169, in response to which sensor tube 360 actuates the switch 230. The switch 230 is coupled to the microcontroller 400 and is configured to transmit the sensor signal reflective of the sensor tube 360 being engaged by the articulating loading unit 169. The microcontroller 400 then determines that the loading unit 169 is articulating and activates the articulation mechanism 170. Another type of sensing mechanism is described in a commonly-owned U.S. Pat. No. 5,865,361 entitled "Surgical Stapling Apparatus" the contents of which are hereby incorporated herein in their entirety by reference.

With reference to FIG. 6, the instrument 10 may also include a variable loading unit sensor 370. The loading unit sensor 370 includes a linear potentiometer 290 disposed within the endoscopic portion 140. The linear potentiometer 290 is electrically coupled to a contact 292 disposed on the sensor tube 360. As the loading unit 169 is inserted into the endoscopic portion 140, the sensor tube 360 is moved in the proximal direction. As a result of the movement of the sensor tube 360, the contact 292 slides along the surface of the linear potentiometer 290.

Figure 8:
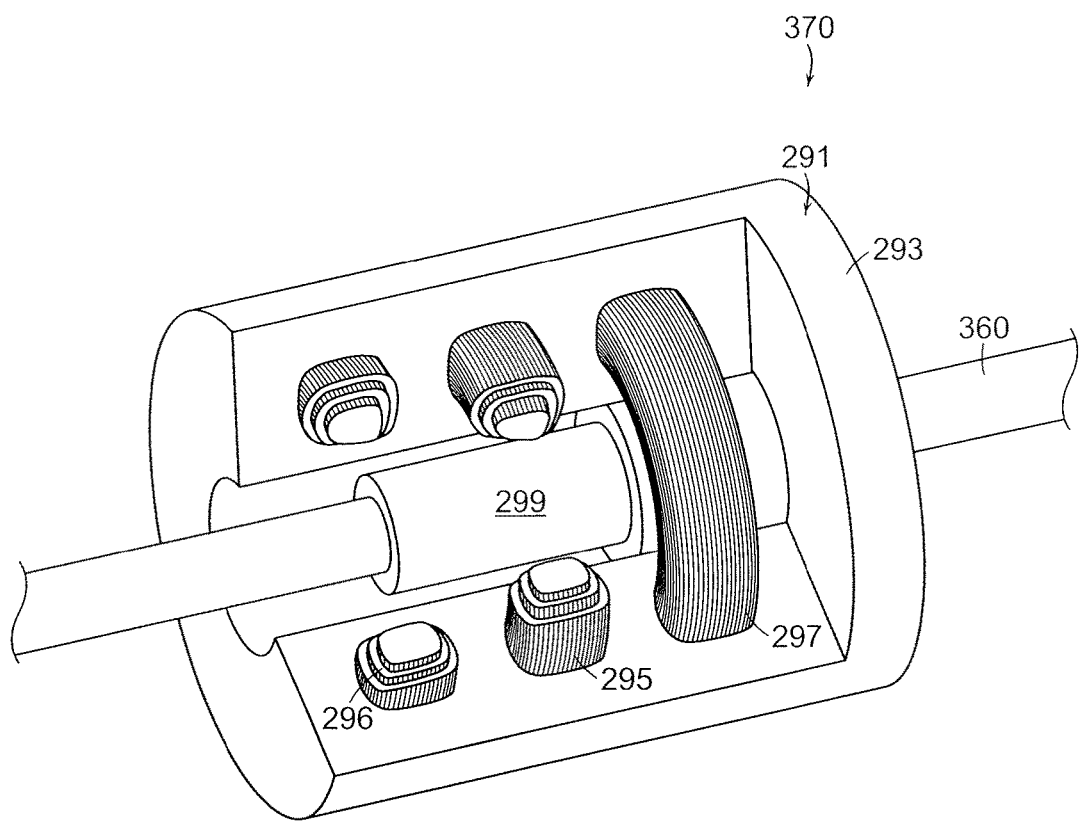
FIG. 8 is a partial perspective sectional view of variable loading unit sensor according to the embodiment of the present disclosure.

In another embodiment shown in FIG. 8, the variable loading unit sensor 370 may also include a linear variable differential transducer (LVDT) 291 disposed about the sensor tube 360. The LVDT 291 includes a transformer 293 having three solenoidal coils arranged about the sensor tube 360, with a center coil 295 being the primary, and the outer coils 296 and 297 being the secondaries. A cylindrical ferromagnetic core 299 may be attached to the sensor tube 360. To measure the displacement of the sensor tube 360, an alternating current is driven through the center coil 295, causing a voltage to be induced in each secondary proportional. As the sensor tube 360 moves, these mutual inductances change due to the shift in the magnetic field brought about by the magnetic core 299 causing the voltages induced in the outer coils 296 and 297 to change. The coils 295, 296 and 297 may be connected in reverse series, so that the output voltage is the difference between the two voltages of the outer coils 296 and 297. When the core 299 is in its central position (e.g., equidistant between the outer coils 296 and 297) equal but opposite voltages are induced in outer coils 296 and 297, so the output voltage is zero.

The variable loading unit sensor 370 is coupled to the microcontroller 400, which is configured to determine the type of the loading unit 169 coupled to the instrument 10 based on the signal from the variable loading unit sensor 370. If the sensor tube 360 is not engaged, such as when the loading unit 169 is not properly inserted, then the variable loading unit sensor 370 is not actuated and the microcontroller 400 does not activate the instrument 10. It is envisioned that various types of loading units 169 may include protrusion 173 and/or extended insertion tips for engaging the sensor tube 360. A non-articulating loading unit may include a protrusion 173 of a first type, while an articulating loading unit 169 may have a protrusion 173 of a second type that is of different dimensions that the first type protrusion 173. In other words, the protrusion 173 of one loading unit 169 is either longer or shorter than the protrusion 173 on another type of loading unit 169. As a result, when inserted, each type of the loading unit 169 engages the sensor tube 360 by a predetermined distance. As a result, the variable loading unit sensor 370 then transmits the corresponding sensor signal corresponding to the displacement of the sensor tube 360 to the microprocessor 400, which then determines the type of the loading unit 169 based thereon. The microcontroller 400 may then activate the articulation mechanism 170 when the loading unit 169 is of articulating type.

The microcontroller 400 may then adjust operating parameters of the instrument 10 to match the inserted loading unit 169 based on the displacement of the sensor tube 360. The adjustable parameters may include firing stroke length, firing speed, degree of articulation and the like. As discussed above, the microcontroller may also prevent actuation of the instrument 10 until the loading unit 169 was loaded into the instrument 10. In another embodiment, the variable loading unit sensor 370 may be disposed along any of the moving sensor parts, such as the sensor tube 360 and the sensor cap 364.

It will be understood that various modifications may be made to the embodiments shown herein. Therefore, the above description should not be construed as limiting, but merely as exemplifications of preferred embodiments. Although specific features of the powered surgical instrument are shown in some of the drawings and not in others, this is for convenience only as each feature may be combined with any or all of the other features in accordance with the aspects of the present disclosure. Other embodiments will occur to those skilled in the art and are within the following claims.

What is claimed:
1. A surgical instrument, comprising:
 a body portion having a distal portion configured to releasably engage a plurality of types of loading units;
 a sensor tube movably disposed within the body portion and configured to engage a loading unit of one of the plurality of types of loading units, the sensor tube including a contact supported thereon;
 a potentiometer disposed within the body portion and electrically coupled to the contact, the contact configured to slide along a surface of the potentiometer, wherein the potentiometer is configured to output a sensor signal corresponding to a predetermined distance traveled by the contact relative to the potentiometer upon engagement of a loading unit with the sensor tube; and
 a microcontroller coupled to the potentiometer and configured to determine a type of a loading unit engaged with the body portion based on the predetermined distance traveled by the contact relative to the potentiometer.

2. The surgical instrument according to claim 1, wherein the potentiometer is configured to transmit the sensor signal to the microcontroller.

3. The surgical instrument according to claim 1, wherein the microcontroller is configured to adjust at least one operating parameter of the surgical instrument based on a type of a loading unit engaged with the body portion.

4. The surgical instrument according to claim 3, wherein the at least one operating parameter is selected from the group consisting of firing stroke length, firing speed, and degree of articulation of a loading unit.

5. A surgical instrument, comprising:
   a body portion having a distal portion configured to releasably engage a plurality of types of loading units;
   a sensor tube including a magnetic member, the sensor tube being movable relative to the body portion and configured to engage a loading unit of one of the plurality of types of loading units;
   a sensor disposed about the magnetic member and configured to be actuated by the magnetic member to output a sensor signal reflective of a loading unit being engaged with the sensor tube; and
   a microcontroller configured to determine a type of a loading unit engaged with the body portion based on a predetermined distance traveled by the magnetic member relative to the sensor upon engagement of a loading unit with the sensor tube.

6. The surgical instrument according to claim 5, wherein the sensor is a linear variable differential transducer including a transformer disposed about the sensor tube.

7. The surgical instrument according to claim 6, wherein the transformer includes a plurality of coils disposed about the sensor tube.

8. The surgical instrument according to claim 5, wherein upon actuation, the sensor signals the microcontroller to activate the surgical instrument.

9. The surgical instrument according to claim 8, wherein the sensor tube is engageable only by a loading unit including an articulating tool assembly.

10. The surgical instrument according to claim 9, further comprising an articulation mechanism.

11. The surgical instrument according to claim 10, wherein upon engagement by a loading unit including an articulating tool assembly, the microcontroller enables the articulation mechanism.

12. A surgical instrument, comprising:
   a body portion having a distal portion configured to releasably engage a plurality of loading unit types;
   a sensor tube including a magnetic member disposed within the body portion, wherein the sensor tube is configured to engage a loading unit of one the plurality of types of loading units and to move a predetermined distance in response to engaging a loading unit;
   a transformer disposed about the sensor tube, wherein the transformer is configured to generate a sensor signal corresponding to a predetermined distance the sensor tube is displaced by a loading unit; and
   a microcontroller configured to determine a type of a loading unit engaged with the body portion based on the predetermined distance the sensor tube is displaced by the loading unit.

13. The surgical instrument according to claim 12, wherein the transformer includes a plurality of coils disposed about the sensor tube.

\* \* \* \* \*